United States Patent [19]
Hu

[11] Patent Number: 5,706,325
[45] Date of Patent: Jan. 6, 1998

[54] EXACT REGIONAL RECONSTRUCTION OF LONGITUDINALLY-UNBOUNDED OBJECTS USING A CIRCLE-AND-LINE CONE BEAM TOMOGRAPHIC SYSTEM

[75] Inventor: Hui Hu, Waukesha, Wis.

[73] Assignee: General Electric Company, Cincinnati, Ohio

[21] Appl. No.: 761,051

[22] Filed: Dec. 5, 1996

[51] Int. Cl.⁶ .................................................. G21K 1/12
[52] U.S. Cl. .............................. 378/4; 378/901; 378/146
[58] Field of Search .............................. 378/4, 901, 146, 378/62

[56] References Cited

U.S. PATENT DOCUMENTS

| | | | |
|---|---|---|---|
| 5,400,255 | 3/1995 | Hu | 364/413.19 |
| 5,499,283 | 3/1996 | Toki | 378/146 |

OTHER PUBLICATIONS

"Practical Cone-Beam Algorithm", by L.A. Feldkamp, L.C. Davis and J.W. Kress, J. Opt. Soc. Am. A/vol. 1, No. 6/Jun. 1984, pp. 612–619.

"CT Cone Beam Image Reconstruction with Circle and Line Scan Path", Patent Application, Hui Hu, No. 15CT–04311, Serial No. 08/673,453, filed Jun. 25, 1996.

*Primary Examiner*—Don Wong
*Attorney, Agent, or Firm*—Andrew C. Hess; Nathan D. Herkamp

[57] ABSTRACT

In a computed tomography imaging system, wherein a longitudinally-unbounded object is oriented with respect to a source of cone beam radiation and a detector array, a method is provided for reconstructing an image of the longitudinally-unbounded object. Initially, relative movement between a longitudinally-unbounded object and the cone beam source is established along at least one circular scan path and at least one linear component. The cone beam is operated to irradiate measurable regions of the object while a prescribed orbit is traversed, to project an image of the longitudinally-unbounded object as cone beam data, onto the detector array. A scan field of view is defined, relative to the cone beam geometry. An error propagation distance in a Z direction is determined for the scan. The definition of the scan field of view is then modified, according to error propagation distance, and a set of image reconstruction data is generated, within the modified field of view, from the circular and linear scan paths.

8 Claims, 2 Drawing Sheets

EXACT REGIONAL RECONSTRUCTION OF LONGITUDINALLY-UNBOUNDED OBJECTS USING A CIRCLE-AND-LINE CONE BEAM TOMOGRAPHIC SYSTEM

The Government has rights to this invention pursuant to Contract No. 70NANB5H1148, awarded by the National Institutes of Standards.

TECHNICAL FIELD

The present invention generally pertains to a method and apparatus for significantly improving accuracy and efficiency in computed tomography (CT) cone beam image reconstruction. More particularly, the invention pertains to such method and apparatus wherein cone beam tomography is used to image longitudinally-unbounded objects.

BACKGROUND OF THE INVENTION

In a current computed tomography (CT) system, an x-ray source projects a fan-shaped beam which is collimated to lie within an X-Y plane of a Cartesian coordinate system, termed the "imaging plane." The x-ray beam passes through the object being imaged and impinges upon an array of radiation detectors. The intensity of the transmitted radiation is dependent upon the attenuation of the x-ray beam by the object and each detector produces a separate electrical signal that is a measurement of the beam attenuation. The attenuation measurements from all the detectors are acquired separately to produce the transmission profile.

The source and detector array in a conventional medical CT system are rotated on a gantry within the imaging plane and around the object so that the angle at which the x-ray beam intersects the object constantly changes. In a conventional industrial CT arrangement, the object may be situated on a platform movable rotationally and vertically, while the scanner is fixed. Cone beam imaging has developed as an important technique in constructing a CT image of an object, and in particular a three-dimensional CT image. According to such technique, a cone beam x-ray source irradiates the object as a prescribed orbit or trajectory is traversed, to project an image of the object, in the form of cone beam x-ray data, onto the array of detector elements.

Scan path geometry is an essential consideration in cone beam imaging. It would be desirable, from a standpoint of simplification and symmetry, to scan along a trajectory comprising a circular orbit lying in a single plane. However, it is well known that such orbit is likely to provide insufficient cone beam data for exact image reconstruction.

Various scanning geometries have been developed for image reconstruction from cone beam projection data. In one such geometry, the scan path comprises a circular orbit in combination with a linear path, which is orthogonal to the plane of the circular orbit. Such combination scan path is of great practical interest, since it can be readily implemented by means of conventional CT gantry configuration. Various algorithms are currently available for use in processing cone beam data acquired by scanning along a combined circle and line path, and constructing an image therefrom.

For many applications, the longitudinal extent of the object to be imaged is longer than what can be scanned by the scanner at one time. Such an object is referred to as a longitudinally-unbounded object or rod-like object. One practical consideration in cone beam tomographic system development, then, is how to image the longitudinally-unbounded object when only a portion of it is of interest or can be imaged each time due to the limited detector extent.

It would be desirable, then, to be able to provide an exact regional reconstruction of a longitudinally-unbounded object. The objects, features and advantages of the present invention will become more readily apparent in the following description when taken in conjunction with the appended drawings.

SUMMARY OF THE INVENTION

The present invention provides for a method and apparatus for providing exact and efficient reconstruction of longitudinally-unbounded objects. One important practical consideration in cone beam tomographic system development is how to image the longitudinally-unbounded object when only a portion of it is of interest or can be imaged each time due to the limited detector extent.

The present invention applies circle-and-line cone beam tomography to image a longitudinally-unbounded object. In a CT imaging system, or other arrangement wherein a source of cone beam radiation, together with a planar detector array, are mounted for selective movement with respect to an object, a method is provided for reconstructing an image of the object from acquired projected data. Initially, relative movement between a longitudinally-unbounded object and the cone beam source is established along at least one circular scan path and at least one linear scan path. The cone beam is operated to irradiate measurable regions of the object while a prescribed orbit is traversed, to project an image of the longitudinally-unbounded object as cone beam data, onto the detector array. A scan field of view is defined, relative to the cone beam geometry. An error propagation distance in a Z direction is determined for the scan. Then the definition of the scan field of view, is modified, according to error propagation distance, and a set of image reconstruction data is generated, within the modified field of view, from the at least one circular scan path and the at least one linear scan path.

In the drawings as hereinafter described, a preferred embodiment is depicted; however, various other modifications and alternative constructions can be made thereto without departing from the true spirit and scope of the invention.

BRIEF DESCRIPTION OF THE DRAWINGS

The novel features of the invention are set forth with particularity in the appended claims. The invention itself, however, both as to organization and method of operation, together with objects and advantages thereof, may best be understood by reference to the following description taken in conjunction with the accompanying drawings in which:

DETAILED DESCRIPTION OF THE INVENTION

Figure 1:
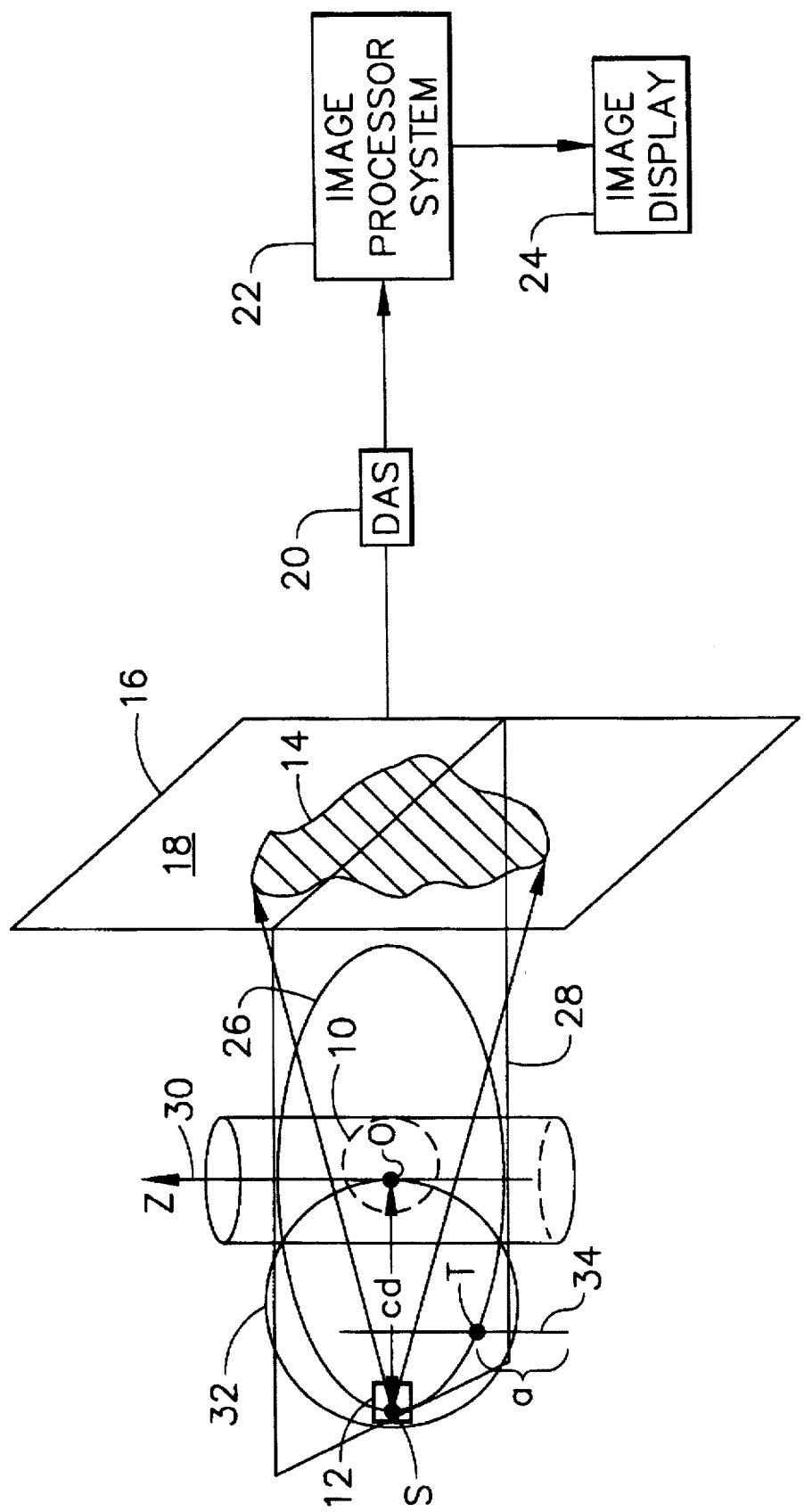
FIG. 1 is schematic diagram illustrating principal elements of a CT cone beam imaging system and an associated circle-and-line scan path.

The circle-and-line orbit consists of a circle and a finite, orthogonal line. A set of cone beam projections from the circular orbit and the linear orbit are characterized as $P_\phi(Y,Z)$ and $\hat{P}_{Z_o}(Y,Z)$ respectively. Let $P_{\Phi \text{ or } Z_o}(Y,Z)$ denote the weighted projection which is derived as follows:

$$P_{\Phi \text{ or } Z_o}(Y,Z) = \frac{d}{\sqrt{d^2 + Y^2 + Z^2}} \hat{P}_{\Phi \text{ or } Z_o}(Y,Z) \qquad 1$$

The present invention is based on the discovery that for the circle-and-line orbit, any function to be reconstructed can be expressed as the sum of three terms:

$$f(r) = f_{c0}(r) + f_{c1}(r) + f_l(r) \qquad 2$$

The $f_{c0}(r)$ term, computed from circularly scanned data, corresponds to the Feldkamp reconstruction (Equation 3 below), explained in an article by L. Feldkamp, L. Davis and J. Kress entitled "Practical Cone-Beam Algorithm," J.Opt.Soc.Am., pp 612–619, 1984. U.S. Pat. No. 5,400,255, totally incorporated herein by reference, teaches how to compute $f_{c1}(r)$, formulated in Equation 4 below, from the circularly scanned cone beam projection data, and proposes to estimate $f_l(r)$. Co-pending, commonly assigned U.S. patent application, Ser. No. 08/673,453, filed Jun. 25, 1996, totally incorporated herein by reference, further teaches how to accurately compute $f_l(r)$ from the linearly scanned cone beam projection data using Equations 5. $(Y_o, Z_o)$ from back-projections are derived from Equation 6 below.

$$f_{c0}(\vec{r}) = \frac{1}{4\pi^2} \oint d\Phi \frac{d^2}{(d + \vec{r} \cdot \hat{x}')^2} \left[ \int dY \int dZ P_\Phi(Y,Z) g_y(Y - Y) g_z(Z - Z) \right]_{Y=Y_o, Z=Z_o} \qquad 3$$

$$f_{c1}(\vec{r}) = -\frac{1}{4\pi^2} \oint d\Phi \frac{z}{(d + \vec{r} \cdot \hat{x}')^2} \left[ -\frac{\partial}{\partial Z} \int P_\Phi(Y,Z) dY \right]_{Z=Z_o} \qquad 4$$

$$f_l(\vec{r}) = -\frac{1}{4\pi^2 (d + \vec{r} \cdot \hat{x}')} \int dz_o \int_{\Theta=0}^{\pi} d\Theta H(z_o, \Theta, l)_{l=Y_o \sin\Theta + Z_o \cos\Theta} \qquad 5a$$

where $$H(z_o, \Theta, l) = \cos\Theta w(z_o, \Theta, l) \left( \frac{d^2 + l^2}{d^2} \frac{\partial^2 \Sigma_{z_o}(l,\Theta)}{\partial l^2} + \frac{2l}{d^2} \frac{\partial \Sigma_{z_o}(l,\Theta)}{\partial l} \right) \qquad 5b$$

$$\Sigma_{z_o}(l,\Theta) = \int \int P_{z_o}(Y,Z) \delta(Y\sin\Theta + Z\cos\Theta - l) dY dZ \qquad 5c$$

$$w(z_o, \Theta, l) = \begin{cases} 1 & \text{when } 2 l z_o \cos\Theta + z_o^2 \cos^2\Theta - d^2 \sin^2\Theta > 0 \\ 0 & \text{otherwise} \end{cases} \qquad 5d$$

$$Y_o = \frac{d \vec{r} \cdot \hat{y}'}{d + \vec{r} \cdot \hat{x}'} \qquad Z_o = \frac{d(z - z_o)}{d + \vec{r} \cdot \hat{x}'} \qquad 6$$

The prior art, including the '255 patent and the copending application, do not teach how to image the longitudinally unbounded object. Now, by means of the invention as disclosed herein, the longitudinally-unbounded object can be imaged, section by section, using the same reconstruction algorithm for the circle-and-line orbit described above and in the co-pending application.

Referring to FIG. 1, there are shown the principal components of a cone-beam imaging system for reconstructing and displaying an image of an object 10 contained within a hypothetical cylindrical or longitudinal volume 18. A cone-beam x-ray source 12 is positioned to irradiate object 10, and to thereby project cone-beam data representing an image 14 thereof unto an associated planar detector array 16, comprising a matrix array of discrete detector elements (not shown in detail). The cone-beam projection data is in the form of x-ray photons that penetrate the object and are sensed by the respective detector elements of detector array 16. Thus, planar detector 16 provides cone beam projection data in analog form. Such data is coupled to a Data Acquisition System (DAS) 20, which samples analog data from the respective detector elements and converts the data to digital form for subsequent processing. The digitized projection data is coupled to an image reconstruction processor system 22, which operates on the projection data to reconstruct an image of object 10. The reconstructed image may be presented in viewable form, for example, by means of an image display 24.

FIG. 1 further shows a circular orbit of motion 26 for the cone beam source 12 around the object 10, such orbit lying in a mid-plane 28, i.e., a plane through the cylinder 18. In a typical medical CT arrangement, detector array 16 is constrained to move with source 12, so that object 10 remains positioned therebetween. Cone-beam projection data is acquired by detector array 16 for successive positions or view angles of source 12, as source 12 traverses the circular orbit 26. A Z-axis 30 passes through the object 10, in orthogonal relationship with mid-plane 28, and intersects the mid-plane at a point 0, within object 18. Source 12 can be moved along a linear orbit path 34, which is tangent to the circular orbit 26 at point T, and is oriented in orthogonal relationship with the plane of circular orbit 26 and mid-plane 28.

Figure 2A:
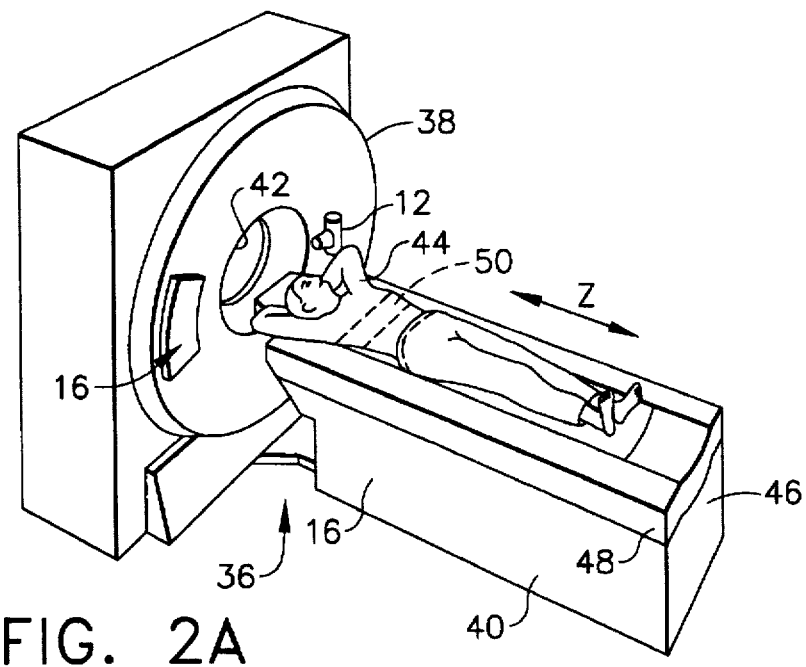
FIGS. 2A and 2B are perspective views illustrating a conventional medical CT imaging system and a conventional industrial CT imaging system, respectively, for use in implementing a CT cone beam imaging system.
Figure 2B:
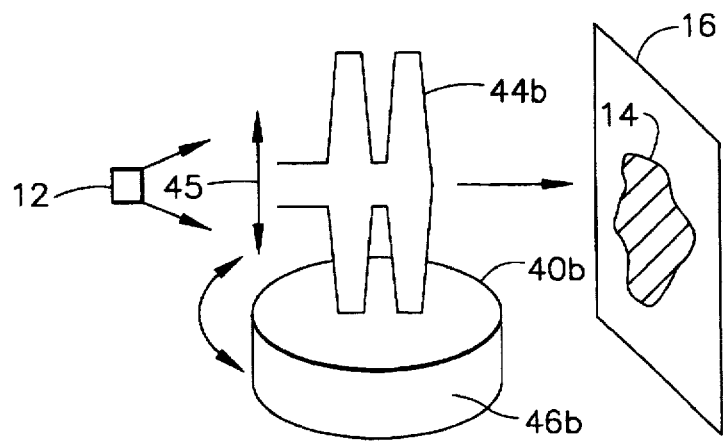

The scan path can be readily implemented by a conventional CT system. Referring to FIG. 2A, there is shown a conventional medical CT system substantially comprising a gantry 38 and a table 40. FIG. 2B illustrates a conventional industrial CT system, with a rotatable platform for holding the object to be scanned. In FIG. 2A, gantry 38 is provided with a bore 42, and table 40a supports a longitudinally-unbounded object 44, such as a patient 44a, for imaging. Of course, it will be obvious to those skilled in the art that the longitudinally-unbounded object may be any of a multitude of known objects including, for example, an aircraft component such as turbine blade 44b in FIG. 2B.

Continuing with FIG. 2A, table 40a comprises a base 46a, and an object support member 48, which is slidable upon base 46a to move the object 44a linearly, along the Z-axis. Thus, table 40a can be operated to insert the object 44a through the bore 42 to position a selected section 50a of the object within the bore, so that an image can be taken therethrough. An object 44a may thus comprise an object section 50a.

In FIG. 2A, source 12 and detector array 16 are mounted on rotatable gantry 38, on opposing sides of the bore 42. Accordingly, a circular orbit 26 may be established by selective rotation of gantry 38. A linear path 34 may be established by linear movement of the object support member 48, while source 12 and array 16 remain stationary. Alternatively, the linear path could be established by mounting the gantry for translational movement along the Z-axis.

In FIG. 2B, a platform 40b comprises a rotatable base 46b for supporting object 44b. This allows for repeated circular scans along a continuous vertical line comprised of repeated linear scans. Platform 40b is also movable in a vertical direction, as indicated by arrow 45 to effect the linear portion of the circle-and-line scan. In a typical industrial CT arrangement, the object 44 moves relative to fixed source 12 and array 16. Of course, it will be obvious to those skilled in the art that in industrial applications, the source may rotate, as in medical CT arrangements.

As can be seen in FIGS. 2A and 2B, for many applications, the longitudinal extent of the object to be imaged is longer than what can be scanned by the scanner at one time, or only a portion of the longitudinally-unbounded object may be of interest. Consequently, as shown in FIG. 2B, repeated circle-and-line scans are taken until the entire longitudinal extent is imaged.

Figure 3:
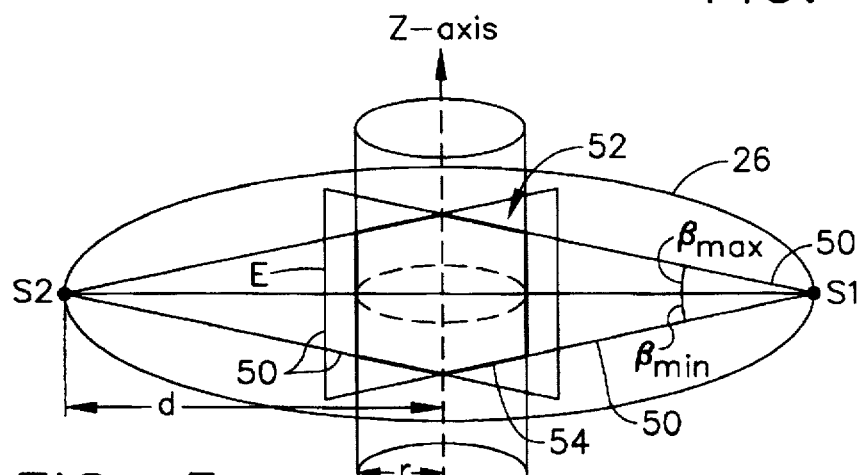
FIG. 3 is a view illustrating the scan field of view of the system, according to the present invention.

Referring now to FIG. 3, a combination of regions 50 indicates the cross-section of the measurable region at a given source location S1. The measurable region is primarily determined by the extent of the detector, indicated by E, and the scan geometry. The scan FOV of the system, indicated as region 52, in accordance with the present invention, can be defined as the overlapping region of all the measurable regions of all source locations on the circular orbit 26. Thus, the scan FOV is defined by a cylinder ended with a cone on each end, whose axes coincide with the axis of rotation. The cross-section of the scan FOV is indicated as area 54. The radius of the cylinder is defined by the detector in-plane extent and scan geometry. The top and bottom cones are defined by the upper and lower cone angles, $\beta_{max}$ and $\beta_{min}$.

In general, the error induced by the longitudinally-unbounded object may propagate inwardly from the top and bottom and contaminate the reconstruction in the top and bottom layers of the FOV. The depth of the contaminated layers, referred to as contamination depth, are determined by the error propagating distance in the Z direction. Different operators employed by different reconstruction algorithms result in different contamination depths. For example, the contamination depth of each term in Equation 1 can be examined. The contamination of the first term, the Feldkamp reconstruction, is zero, since no operation in the Z direction is required. The contamination depth of the second term is a half of the detector Z cell pitch, because a difference operator is applied in the Z direction. Using numerical analysis, it can be proven that the contamination depth of the third term is one detector Z cell pitch. Since the maximum depth of the contaminated layers is one detector Z cell pitch, these contaminated layers can be excluded by slightly modifying the definition of the scan FOV such that its cone ends move inwardly by one detector Z cell pitch at both ends. Thus, with the tomographic system and reconstruction algorithm described in co-pending application Ser. No. 673,453, and within the modified scan FOV, the problem of longitudinally-unbounded objects will never contaminate the reconstruction of f(r). Thus, an exact regional reconstruction of the longitudinally-unbounded object can be achieved with each section defined by moving the cone ends of the scan FOV inwardly by one z-pitch of the detector cell.

With the exact regional reconstruction technique of the present invention, the circle-and-line cone beam scanning system can be implemented by simple rotational scanning and translational scanning. The circular scan can be accomplished by rotating the object to be imaged, so the source-detector assembly can remain fixed and the system alignment undisturbed. The additional truncation problem due to the Region of Reconstruction Interest (ROI) moving beyond the measurable region of the limited-size detector during the translational scan will also be eliminated by the technique of the present invention. The longitudinally-unbounded object can be imaged section by section. The scanning speed can be maximized by choosing the maximized Z displacement between two adjacent sections that minimizes the overlapping without generating a gap between the two sections.

The present invention, therefore, provides for an exact regional reconstruction of a longitudinally unbounded object. The present invention is useful in multitude fields including, for example, computed tomography (CT) cone beam image reconstruction scanning in fields as varying from medical to industrial applications. The present invention, therefore, provides for an exact and computationally efficient reconstruction for general imaging applications.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

I claim:

1. In a computed tomography imaging system wherein a longitudinally-unbounded object is oriented with respect to a source of, cone beam radiation and a detector array, a method for reconstructing an image of the longitudinally-unbounded object, the method comprising the steps of:

establishing relative movement between the longitudinally-unbounded object and the cone beam source along at least one circular scan path and at least one linear scan path;

operating the cone beam to irradiate measurable regions of the object while a prescribed orbit is traversed, to project an image of the longitudinally-unbounded object as cone beam data, onto the detector array;

defining a scan field of view relative to geometry of the cone beam;

determining error propagation distance in a Z direction for the scan;

modifying the definition of the scan field of view, according to error propagation distance; and generating a set of image reconstruction data within the modified scan field of view from the at least one circular scan path and the at least one linear scan path.

2. A method as claimed in claim 1 wherein the step of establishing relative movement between the longitudinally-unbounded object and the cone beam source further comprises the steps of:

fixing the cone beam source in a stationary position;

establishing a circular orbit by selective rotation of the longitudinally-unbounded object;

establishing a linear path by linear movement of the longitudinally-unbounded object.

3. A method as claimed in claim 1 further comprising the step of making repeated circular scans and at least one linear scan until an entire longitudinal extent to be imaged of the longitudinally-unbounded object is imaged.

4. A method as claimed in claim 1 wherein the step of defining a scan field of view further comprises the step of defining the scan field of view by a cylinder ended with a cone on each end, whose axes coincide with an axis of rotation.

5. In a computed tomography imaging system wherein a longitudinally-unbounded object is oriented with respect to a source of cone beam radiation and a detector array, a system for reconstructing an image of the longitudinally-unbounded object, the system comprising:

means for establishing relative movement between the longitudinally-unbounded object and the cone beam source along at least one circular scan path and at least one linear scan path;

a cone beam operated to irradiate measurable regions of the object while a prescribed orbit is traversed, to project an image of the longitudinally-unbounded object as cone beam data, onto the detector array;

a scan field of view relative to geometry of the cone beam;

an error propagation distance in a Z direction for the scan;

means for modifying the definition of the scan field of view, according to error propagation distance; and means for generating a set of image reconstruction data within the modified scan field of view from the at least one circular scan path and the at least one linear scan path.

6. A system as claimed in claim 5 wherein the means for establishing relative movement between the longitudinally-unbounded object and the cone beam source further comprises:

means for fixing the cone beam source in a stationary position;

a circular orbit established by selective rotation of the longitudinally-unbounded object;

a linear path established by linear movement of the longitudinally-unbounded object.

7. A system as claimed in claim 5 further comprising means for making repeated circular scans and at least one linear scan until an entire longitudinal extent to be imaged of the longitudinally-unbounded object is imaged.

8. A system as claimed in claim 5 wherein the scan field of view comprises a scan field of view defined by a cylinder ended with a cone on each end, whose axes coincide with an axis of rotation.

* * * * *